(12) United States Patent
Sugimoto

(10) Patent No.: US 7,860,551 B2
(45) Date of Patent: Dec. 28, 2010

(54) MAGNETIC RESONANCE DIAGNOSTIC APPARATUS

(75) Inventor: Hiroshi Sugimoto, Utsunomiya (JP)

(73) Assignees: Kabushiki Kaisha Toshiba, Minato-Ku, Tokyo (JP); Toshiba Medical Systems Corporation, Otawara-Shi, Tochigi-Ken (JP)

(*) Notice: Subject to any disclaimer, the term of this patent is extended or adjusted under 35 U.S.C. 154(b) by 1461 days.

(21) Appl. No.: 11/212,849

(22) Filed: Aug. 29, 2005

(65) Prior Publication Data
US 2006/0047198 A1  Mar. 2, 2006

(30) Foreign Application Priority Data
Aug. 30, 2004  (JP)  ............... 2004-250183

(51) Int. Cl.
  *A61B 5/055*  (2006.01)
  *G01V 3/00*  (2006.01)
(52) U.S. Cl. ...................... 600/410; 324/309
(58) Field of Classification Search ......... 600/407–411, 600/422, 415; 324/307, 318, 309, 314, 320; 174/374
See application file for complete search history.

(56) References Cited

U.S. PATENT DOCUMENTS

| | | | | |
|---|---|---|---|---|
| 4,134,213 A * | 1/1979 | Kushmuk | ................ | 33/512 |
| 4,487,276 A * | 12/1984 | Swersey et al. | ............ | 177/1 |
| 6,226,881 B1 * | 5/2001 | Landauer | ................ | 33/515 |
| 6,841,999 B2 * | 1/2005 | Arneth et al. | ............ | 324/309 |
| 7,078,901 B2 * | 7/2006 | Feiweier et al. | .......... | 324/318 |
| 7,145,338 B2 * | 12/2006 | Campagna et al. | ........ | 324/318 |
| 7,164,268 B2 * | 1/2007 | Mugler et al. | ............ | 324/307 |
| 2002/0087066 A1 | 7/2002 | Hellinger | | |
| 2002/0161294 A1 | 10/2002 | Drobnitzky | | |
| 2003/0098687 A1 | 5/2003 | Arneth et al. | | |
| 2003/0098688 A1 | 5/2003 | Brinker et al. | | |
| 2005/0264288 A1 * | 12/2005 | Campagna et al. | ........ | 324/309 |

FOREIGN PATENT DOCUMENTS

| | | |
|---|---|---|
| DE | 10 2005 011 156 A1 | 10/2005 |
| JP | 3-284241 | 12/1991 |
| JP | 5-317287 | 12/1993 |

OTHER PUBLICATIONS

Specific Absorption Rates and Induced Current Densities for an Anatomy Based Model of the Human for exposure of Time Varying Magnetic OF MRI Chen et all.*
eSTIMATION of Heat Transfer Temperature Rise in Partial-Body Regions During mr Procedures:An analytical approach with respect to safety consideration Brix et all.*
International Standard, IEC 60601-2-33, May 2002, Medical electrical equipment, Part 2-33: Particular requirements for the safety of magnetic resonance equipment for medical diagnosis.
European Search Report—Dec. 23, 2005.

* cited by examiner

*Primary Examiner*—Eric F Winakur
*Assistant Examiner*—Lawrence N Laryea
(74) *Attorney, Agent, or Firm*—Nixon & Vanderhye PC

(57) ABSTRACT

A magnetic resonance diagnostic apparatus includes an input unit which inputs information associated with the physique of a subject to be examined and information associated with an imaging region, a calculating unit which calculates a partial body SAR associated with a partial body including the imaging region on the basis of the input information associated with the physique and the input information associated with the imaging region, and a display unit which displays the calculated partial body SAR.

27 Claims, 4 Drawing Sheets

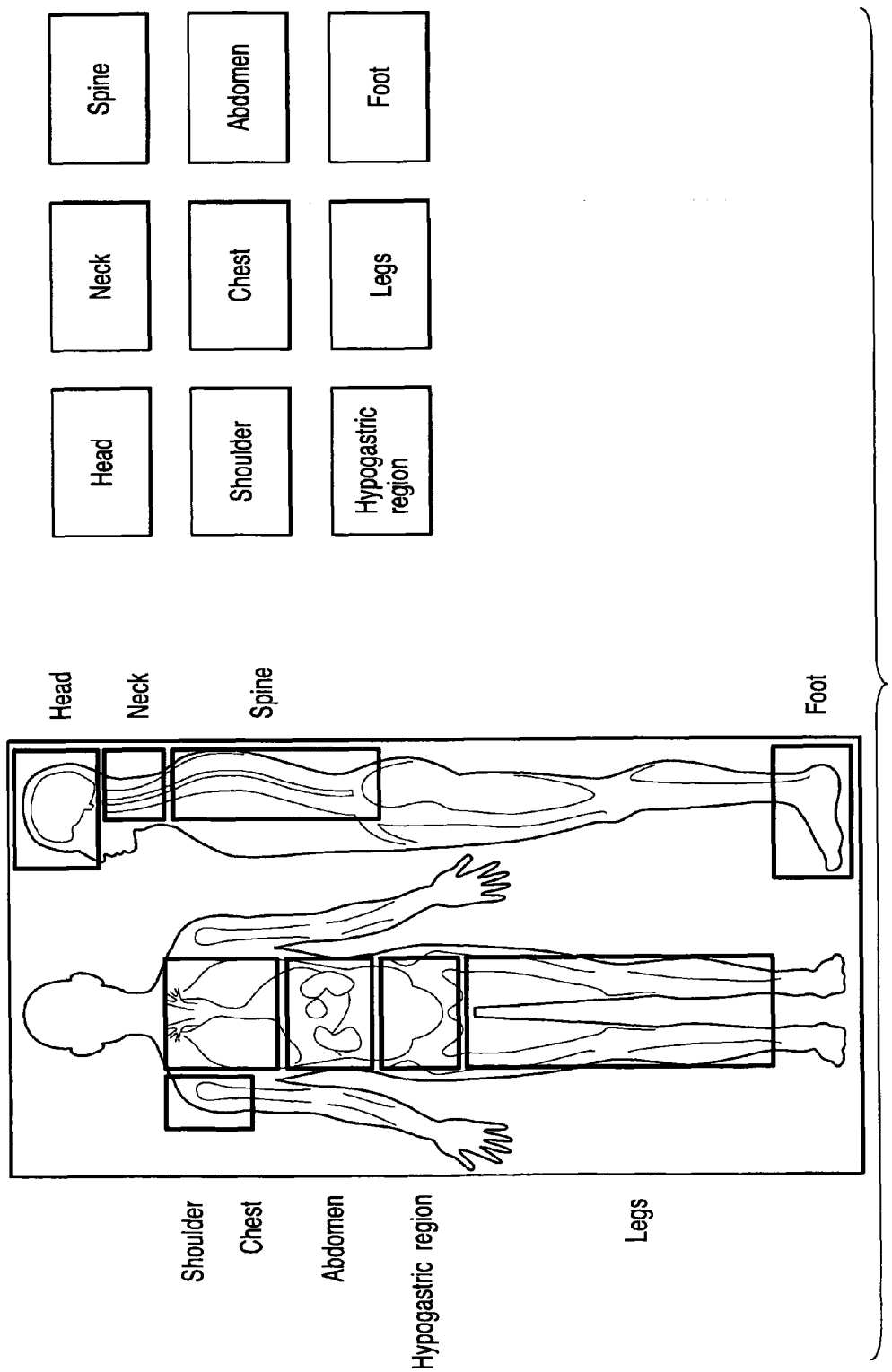
F I G. 5

MAGNETIC RESONANCE DIAGNOSTIC APPARATUS

CROSS-REFERENCE TO RELATED APPLICATIONS

This application is based upon and claims the benefit of priority from prior Japanese Patent Application No. 2004-250183, filed Aug. 30, 2004, the entire contents of which are incorporated herein by reference.

BACKGROUND OF THE INVENTION

1. Field of the Invention

The present invention relates to a magnetic resonance diagnostic apparatus having a safety management function based on SARs (Specific Absorption Rate).

2. Description of the Related Art

A magnetic resonance diagnostic apparatus (to be referred to as an MRI apparatus hereinafter) is designed to apply a high-frequency magnetic field for causing magnetic resonance to an imaging region by using a transmission high-frequency coil. The resonance frequency of a high-frequency magnetic field is proportional to the static field strength of the MRI apparatus. If, for example, the apparatus has a static field strength of 1.5 T, the resonance frequency is 63.8 MHz. It is known that a high frequency in this frequency region heats a subject to be examined and raises his/her body temperature. In general, concerning the human body, an increase in body core temperature is more problematic in terms of safety than an increase in skin temperature. When an increase in the body core temperature of the human body exceeds 1° C., a trouble may occur. For this reason, the upper limit value of temperature rise in terms of safety is set to 1° C., and the upper limit value of SAR (Specific Absorption Rate), which is the high-frequency output absorbed by 1-kg tissue, is set in IEC standards (IEC 60601-2-33 Second Edition: Particular requirements for the safety of magnetic resonance equipment for medical diagnosis) or JIS standards (JIS Z4951 "Particular requirements for the safety of magnetic resonance equipment for medical diagnosis"). For example, in the normal operating mode based on IEC standards, the upper limit of SAR value with respect to the whole body is 2 W/kg, and the upper limit value of SAR value with respect to the head is 3.2 W/kg.

For example, before imaging operation, an operator inputs the weight (kg) of a patient as part of patient information such as the patient name, age, and sex through the console. The operator positions a subject P to be examined in a magnetic gantry 2 of an MRI apparatus, and applies high-frequency waves from a high-frequency amplifier 3 to the subject P through a transmission high-frequency coil 4 to set high-frequency conditions for obtaining an MR signal optimal for an imaging region of the subject P. The operator then performs imaging operation using the conditions. Since the difference between the high-frequency output which was applied when the high-frequency conditions were set and the high-frequency output measured under the condition of no subject is the high-frequency output (W) absorbed by the subject, the quotient of the output value by the patient's weight input in advance is a whole body SAR value (W/kg). The MRI apparatus calculates a whole body SAR value before imaging operation, and displays it on the screen of a console (1). If the obtained SAR value exceeds the upper limit value in the above safety standards, a corresponding warning is displayed on the screen of the console (1). The operator then changes the imaging conditions or switches the current mode to an upper-level operating mode.

In a general example of changing the imaging conditions, the operator may make setting again to decrease the initially set number of multi-slices. In this case, the necessary imaging region cannot be covered by one set of multi-slices, and hence two or more imaging operations are required, resulting in an increase in overall MRI examination time. With regard to the switching of operation modes, a first level controlled operating mode and secondary level controlled operating mode are defined as well as the normal operation mode by the safety standards. Medical determination on this switching operation is performed in consideration of the relationship between potential risks and merits for the patient. For example, in the primary level controlled operating mode, the upper limit value of whole body SAR value is 4 W/kg.

The axial length of the transmission high-frequency coil of a conventional MRI apparatus is about 50 to 60 cm. As an SAR value for adults, aside from children, the SAR value obtained by dividing a high-frequency output by the weight of the whole body including a portion to which no high-frequency output is applied does not necessarily coincide with the SAR value of the partial body to which a high-frequency output is actually applied. On the other hand, as high-speed imaging methods and high-field MRI apparatuses have been developed, pulse sequences for obtaining MR images which ensure higher diagnostic performance require higher SAR values.

According to IEC standards (IEC 60601-2-33, 2nd Edition) revised in 2002, the following is defined as a partial body SAR:

In case of normal operation mode:

$$\text{partial body SAR} = 10(W/kg) - (8(W/kg) \times (\text{weight of part to which high-frequency waves are applied}) / (\text{weight of patient}))$$

An SAR value in the range of 2 W/kg to 10 W/kg is set as an upper limit in accordance with the ratio between the weight of a part of a patient to which high-frequency waves are applied and the weight of the patient.

A conventional method of performing management on the basis of only whole body SARs cannot cope with definition of this partial body SAR, and hence cannot provide diagnosis information with higher accuracy. Furthermore, even if the transmission high-frequency coil is reduced in length to be directed to a specific region such as the heart so as to limit the area to which high-frequency waves are to be applied, a conventional method, e.g., the method disclosed in Jpn. Pat. Appln. KOKAI Publication No. 5-317287, cannot cope with this.

BRIEF SUMMARY OF THE INVENTION

It is an object of the present invention to improve the accuracy of safety management using partial body SARs in a magnetic resonance diagnostic apparatus.

According to a first aspect of the present invention, there is provided a magnetic resonance diagnostic apparatus comprising an input unit which inputs information associated with a physique of a subject to be examined and information associated with an imaging region, a calculating unit which calculates a partial body SAR associated with a partial body including the imaging region on the basis of the input information associated with the physique and the input information associated with the imaging region, and a display unit which displays the calculated partial body SAR.

According to a second aspect of the present invention, there is provided a magnetic resonance diagnostic apparatus comprising an RF coil which generates an RF pulse, a calculating unit which calculates a partial body SAR associated with a part of a subject to be examined which corresponds to a transmission range of the RF pulse which is unique to the RF coil, and a display unit which displays the calculated partial body SAR.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a view showing an imaging region selection window in this embodiment.

DETAILED DESCRIPTION OF THE INVENTION

An embodiment of a magnetic resonance diagnostic apparatus (MRI apparatus) according to the present invention will be described in detail below with reference to the views of the accompanying drawing.

Figure 1:
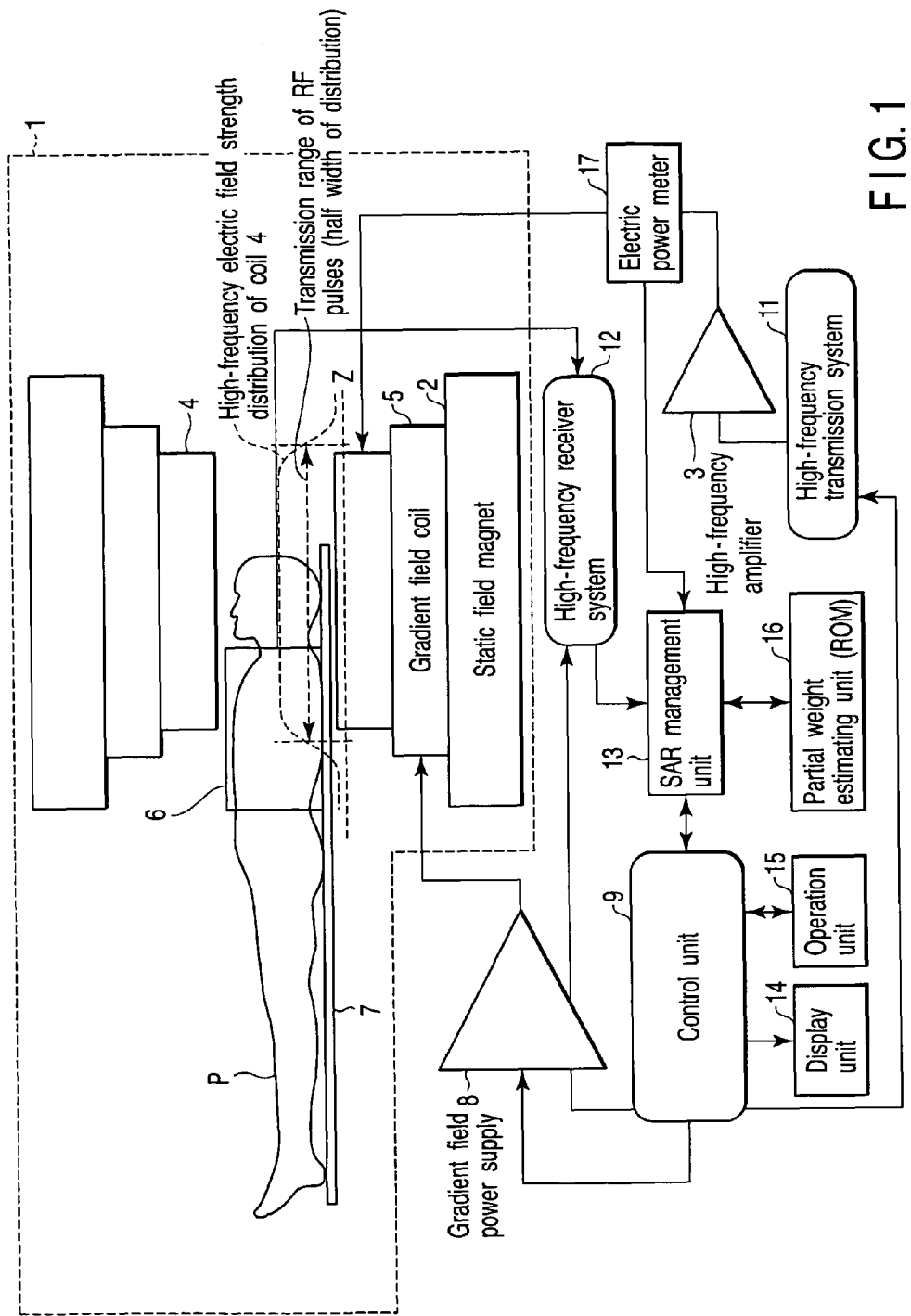
FIG. 1 is a block diagram showing the schematic arrangement of an MRI apparatus according to this embodiment.

FIG. 1 is a block diagram showing the schematic arrangement of an MRI apparatus according to this embodiment. A static field magnet 2, gradient field coil 5, and transmission high-frequency coil 4 are provided in a cylindrical magnetic gantry 1. For the sake of convenience, assume that the z-axis coincides with the longitudinal direction of the cylindrical gantry, and the x-axis and y-axis coincide with the horizontal and vertical directions, respectively. The static field magnet 2 is formed by using, for example, a 1.5-T superconductive magnet and forms a static field parallel to the z-axis. The gradient field coil 5 is placed in the static field magnet 2 to form a cylindrical assembly and generates an x-axis gradient field, y-axis gradient field, and z-axis gradient field. Note that the shape and type of each assembly are not limited. The transmission high-frequency coil 4 is placed inside the gradient field coil 5 to form, for example, a cylindrical shape, and generates a high-frequency magnetic field. As the transmission high-frequency coil 4, a transmission/receiver high-frequency coil can be used. An MR signal generated by magnetic resonance is detected by a receiver high-frequency coil 6 placed around a subject P to be examined. Note that the bed has a top 7, and the subject P placed on the top 7 is inserted into the imaging space (the area in which an imaging magnetic field is formed) in the magnetic gantry 1.

The gradient field coil 5 is connected to a control unit 9 through a gradient field power supply 8. The gradient field power supply 8 supplies a current necessary for causing the gradient field coil 5 to generate a magnetic field. The magnitude of the current (the strength of the magnetic field), the timing of current supply (the application timing of a magnetic field), and the like are controlled by control signals from the control unit 9. The transmission high-frequency coil 4 is connected to the control unit 9 through a high-frequency amplifier 3 and high-frequency transmission system 11. An electric power meter 17 for measuring a transmission high-frequency output is provided between the transmission high-frequency coil 4 and the high-frequency amplifier 3. The receiver high-frequency coil 6 is connected to the control unit 9 through a high-frequency receiver system 12. The high-frequency amplifier 3 is driven when a high-frequency magnetic field is to be transmitted from the transmission high-frequency coil 4 to the subject P. The high-frequency receiver system 12 is driven when an MR signal from the subject P is to be detected through the receiver high-frequency coil 6.

A display unit 14, operation unit 15, and SAR management unit 13 are connected to the control unit 9. A physique is determined from a weight and height. A partial weight of an imaging region is almost determined from a physique. Therefore, a table in which standard partial weights are made to correspond to weights, heights, and imaging regions is generated, and is stored in a partial weight estimating unit 16 typically comprising a ROM.

The partial weight estimating unit 16 estimates the partial weight of an imaging region from information associated with a physique (weight information and height information) input from the operation unit 15 and the imaging region input from the operation unit 15.

The SAR management unit 13 calculates a partial body SAR associated with the imaging region on the basis of the partial weight estimated by the partial weight estimating unit 16, the transmission high-frequency output measured by pre-transmission of a high-frequency pulse (RF pulse) using the electric power meter 17 in the presence of the subject P, the number of high-frequency pulses in the pulse sequence set through the operation unit 15, and the like.

The SAR management unit 13 calculates the upper limit value of partial body SAR associated with the imaging region on the basis of the partial weight estimated by the partial weight estimating unit 16 from the imaging region and the weight input from the operation unit 15. The SAR management unit 13 compares the partial body SAR with the upper limit value.

Note that the SAR management unit 13 may directly obtain a partial body SAR associated with an imaging region, without obtaining a partial weight, on the basis of the information of physique (weight information and height information) input from the operation unit 15, the imaging region input from the operation unit 15, the transmission high-frequency output measured by pre-transmission of a high-frequency pulse (RF pulse) using the electric power meter 17 in the presence of the subject P, and the number of high-frequency pulses in the pulse sequence set through the operation unit 15. A table in which partial body SARs are made to correspond to weights, heights, imaging regions, transmission high-frequency outputs, and the numbers of high-frequency pulses is generated in advance, and is typically provided through a ROM.

The SAR management unit 13 causes the display unit 14 to display the result of comparison between the partial body SAR and the upper limit value and the like. The display unit 14 displays MR images of the subject P, imaging conditions, the whole body or partial body SAR, the result of comparison between the SAR and the upper limit value, and information indicating recommended changes of imaging conditions for decreasing the SAR when the calculated SAR value exceeds the upper limit value. The information indicating the recommended changes of imaging conditions includes a decrease in the number of multi-slices in the pulse sequence, an increase in slice thickness in the pulse sequence, a change in pulse sequence, and the like.

Figure 2:
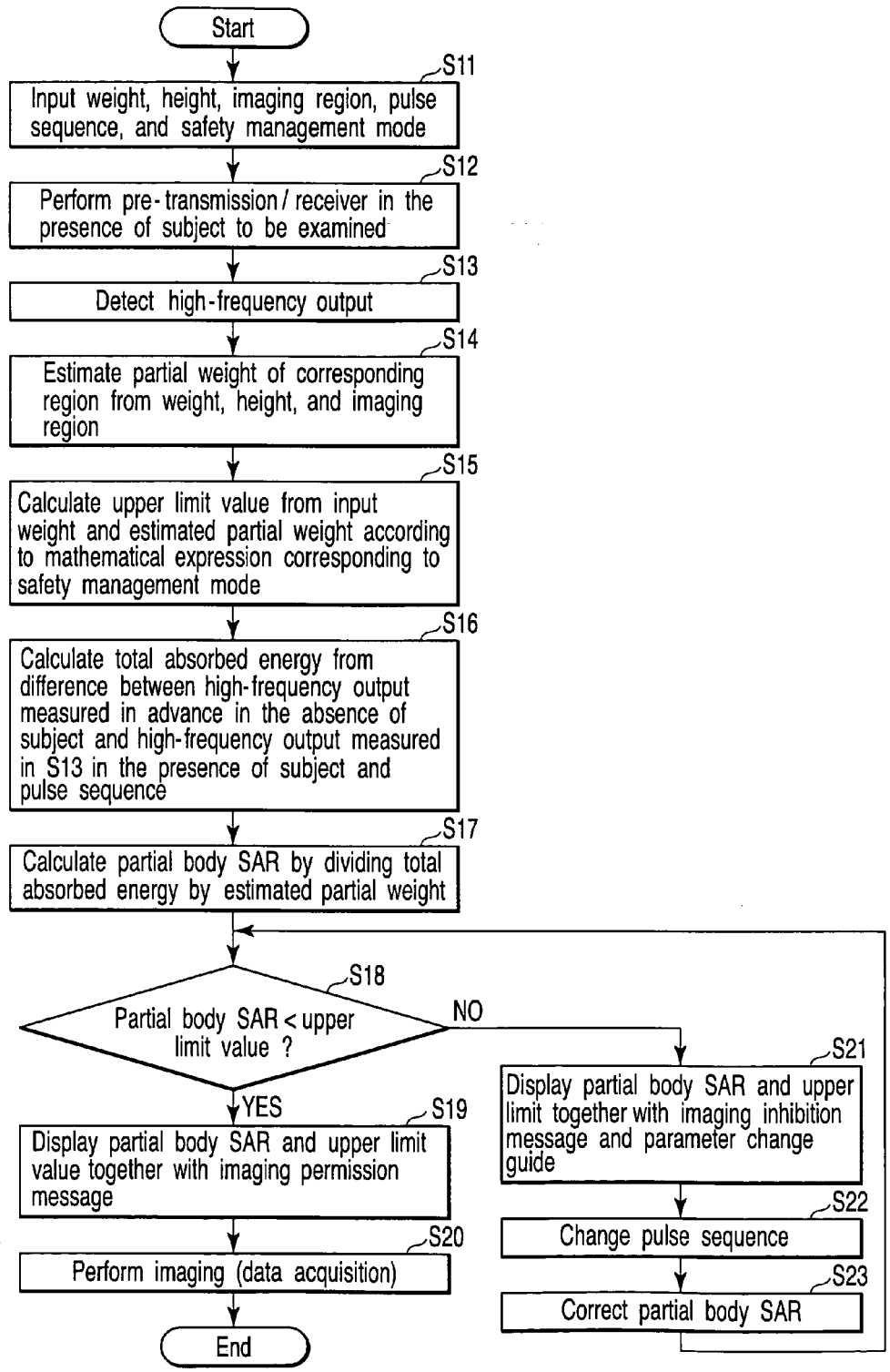
FIG. 2 is a flowchart showing the flow of SAR managing operation in this embodiment.

SAR managing operation in this embodiment will be described below with reference to FIG. 2. The operator inputs patient information, imaging conditions, and safety management mode with the operation unit 15 before imaging operation (S11). The patient information includes a patient name, age, sex, and physique information. The physique information includes the patient's weight and height. These pieces of information may already have been input at the time of reservation of examination. If the weight and height are written on a clinical chart or the like, these values are directly input through the keyboard of the operation unit 15. If no such information is available, a weight and height are measured by a weight scale and anthropometer or the like before MR examination, and are numerically input through the keyboard of the operation unit 15. Alternatively, a plurality of standard models with different physiques may be prepared, and the operator may select a single standard model approximating the subject from the plurality of standard models instead of inputting a weight and height.

Imaging conditions include an imaging region, the type of pulse sequence, the number of multi-slices, slice thickness, and the like. These conditions may be designated when an examination is requested from a doctor in charge of a given patient, or determined for each facility, or determined by a doctor at the time of imaging operation. The operator inputs necessary imaging conditions in accordance with such a situation. The safety management mode includes the normal operation mode, first level controlled operating mode, and second level controlled operating mode as choices, in which different methods are used to calculate the upper limit value of SAR. One of these modes is selected.

After the input operation of these conditions (S11), the subject P is placed on the top 7 of the bed, inserted into the magnetic gantry 1, and positioned for imaging operation. In general, the center of the imaging region is aligned with the center of the magnetic gantry 1. At the position set before imaging operation, a search is made for optimal conditions for transmission high-frequency pulses (RF pulses) under the control of the control unit 9. A plurality of RF pulses with different time integral values are intermittently applied to the subject P, and an MR signal from the subject P is received through the receiver high-frequency coil 6 every time an RF pulse is applied (S12). The time integral value of an RF pulse corresponding to an MR signal having the highest intensity which generates a magnetization spin with a flip angle closest to 90° being tilted is selected as an optimal condition. In addition, a transmission high-frequency output is measured by the electric power meter 17 every time an RF pulse is applied (S13). The transmission high-frequency output measured when an RF pulse corresponding to an MR signal with the highest intensity is applied is selected.

Following steps S12 and S13, a partial weight is estimated from the weight, height, and imaging region input from the operation unit 15 (S14). In practice, the partial weight estimating unit 16 supplies a partial weight corresponding to the weight, height, and imaging region input from the operation unit 15 to the SAR management unit 13. In step S15, the SAR management unit 13 calculates the upper limit value of partial body SAR of the imaging region from the weight input from the operation unit 15 and the estimated partial weight according to a mathematical expression corresponding to the safety management mode selected in step S11. The SAR management unit 13 calculates, as the absorbed energy of the subject upon application of a single 90° high-frequency pulse, the difference between the high-frequency output measured in advance in the absence of a subject to be examined, i.e., without the subject P being inserted into the gantry 1, and the transmission high-frequency output of an RF pulse searched out in the presence of a subject to be examined, i.e., with the subject P being inserted into the gantry 1. The SAR management unit 13 calculates the total absorbed energy of the subject from the absorbed energy upon application of a single 90° high-frequency pulse, and the numbers of 90° high-frequency pulses, 180° high-frequency pulses, and other high-frequency pulses in the pulse sequence designated in step S11 (S16). The SAR management unit 13 calculates a partial body SAR corresponding to an imaging portion by dividing the total absorbed energy by the estimated partial weight (S17).

According to the above description, the partial weight of an imaging region is estimated, and a partial body SAR is calculated from the partial weight. However, the weight of a part of a subject to be examined which is accommodated in a range in which RF pulses are substantially transmitted, instead of an imaging region, may be estimated, and a partial body SAR may be calculated by dividing the total absorbed energy by the weight of the part. The range in which RF pulses are substantially transmitted is typically set to a range, of the spatial distribution of high-frequency electric field strengths concerning a body axis Z unique to the transmission high-frequency coil 4 in FIG. 1, in which the strength exceeds a predetermined strength, e.g., a range defined by a half width.

The SAR management unit 13 compares the partial body SAR calculated in step S17 with the upper limit value calculated in step S15 (S18). If the partial body SAR is less than the upper limit value (YES), the control unit 9 causes the display unit 14 to display the partial body SAR calculated in step S17, the upper limit value calculated in step S15, and an imaging permission message (S19), and waits for the input of a trigger for the execution of a pulse sequence from the operation unit 15. When a trigger for the execution of a pulse sequence is input from the operation unit 15, the pulse sequence in step S11 is executed with optimized high-frequency pulses (S20).

If the partial body SAR is equal to or more than the upper limit value (NO), the control unit 9 causes the display unit 14 to display the partial body SAR calculated in step S17, the upper limit value calculated in step S15, an imaging inhibition message, and a pulse sequence change guide (S21). The pulse sequence change guide includes the changing of the pulse sequence itself to another type of pulse sequence, a decrease in the number of multi-slices, and an increase in slice thickness. When the pulse sequence is changed through the operation unit 15 (S22), a partial body SAR is re-calculated (corrected) by the same calculation method as that in step S17 in accordance with the changed pulse sequence (S23).

Steps S21 to S23 are repeated until the partial body SAR corrected in step S23 becomes less than the upper limit value.

A method of obtaining an SAR value in this embodiment will be described in detail below. The definition of an SAR and its upper limit value in safety standards for an MRI apparatus will be described first by taking IEC 60601-2-33, 2nd Edition as an example. An SAR is a high-frequency output per unit mass absorbed by a subject to be examined, and is measured in [W/kg]. SARs are classified into a whole body SAR, partial body SAR, head SAR, and local SAR according to imaging regions. A whole body SAR is used for imaging of the whole body; a head SAR, for imaging of the head; and a local SAR, for imaging of a small region of the body by using a transmission/receiver surface coil and the like, in which case alone, an average value through 10g body tissue is used. A partial body SAR is an item added from the second edition of IEC standard, and is the average value of weights of body portions exposed to the transmission high-frequency coil. The upper limit values of these SARs are set as follows. For example, in the normal operation mode, the upper limit value of whole body SAR is 2 W/kg, the upper limit value of head SAR is 3.2 W/kg, the upper limit value of local SAR is 10 W/kg for the head and core, and 20 W/kg for the limbs, and the upper limit value of partial body SAR is given by 10−8×(weight of portion to be imaged/weight) [W/kg]

As operation modes, in addition to the normal operation mode, the primary level controlled operating mode and secondary level controlled operating mode are defined, and an SAR upper limit value is set for each mode. These upper limit values are set to suppress a temperature rise in the body core due to heating by high-frequency waves, crystalline lenses for which the cooling effect of a blood flow is small to 1° C. or less. When high-frequency waves are applied to the whole body, a whole body SAR value can be obtained by dividing the absorbed high-frequency output by the weight of the subject. When high-frequency waves are applied to only the head, a head SAR value can be obtained by estimating a head weight from standard data concerning human bodies and dividing the high-frequency output by the head weight. The head weights of adults are almost constant, and hence can be estimated relatively easily. In contrast, it is difficult to estimate a partial body SAR value from weight information alone.

In this embodiment, the partial weight of a partial body to which high-frequency waves are applied is estimated from an imaging region (e.g., the chest, abdomen, hypogastric region, or femoral region) and the height of the subject as well as the weight, together with standard human body data, and a partial body SAR value is estimated from the data. Obviously, an error is estimated in the estimated value, it is necessary to set the upper limit value to a lower value on the safety side in consideration of the error. In the normal imaging mode, therefore, although the upper limit value of whole body SAR is 2 W/kg when high-frequency waves are applied to the whole body, as described above, application of the same high-frequency waves is allowed up to 6 W/kg in terms of safety when high-frequency waves are applied to a partial body corresponding to ½ the weight. This makes it possible to perform faster imaging operation, shorten the imaging time by increasing the number of multi-slices, and obtain accurate diagnosis information by the acquisition of diffusion images with a high b-value or the like. The currently used transmission high-frequency coils are about 60 cm long, and hence it hardly occurs that high-frequency waves are applied to the whole body of any adult, excluding short subjects such as infants and children, at once. It is therefore practical to apply a partial body SAR to such a case. Obviously, however, when the subject is small in statue, and the thoracoabdominal portion is selected as an imaging region, the MRI apparatus may use a whole body SAR.

Height data is input by the following methods:

1) A height is input as a numerical value from the keyboard of the operation unit 15.

2) An appropriate range is selected from a plurality of height ranges displayed in an input window on the operation unit 15 (for example, selected with height range buttons set for every 10 cm, like 150 to 159 cm, 160 to 169 cm,...)

3) A height is electronically input from a patient database in the facility.

The following are methods of measuring a height in an MR room:

1) A height is measured with an anthropometer.

Figure 3:
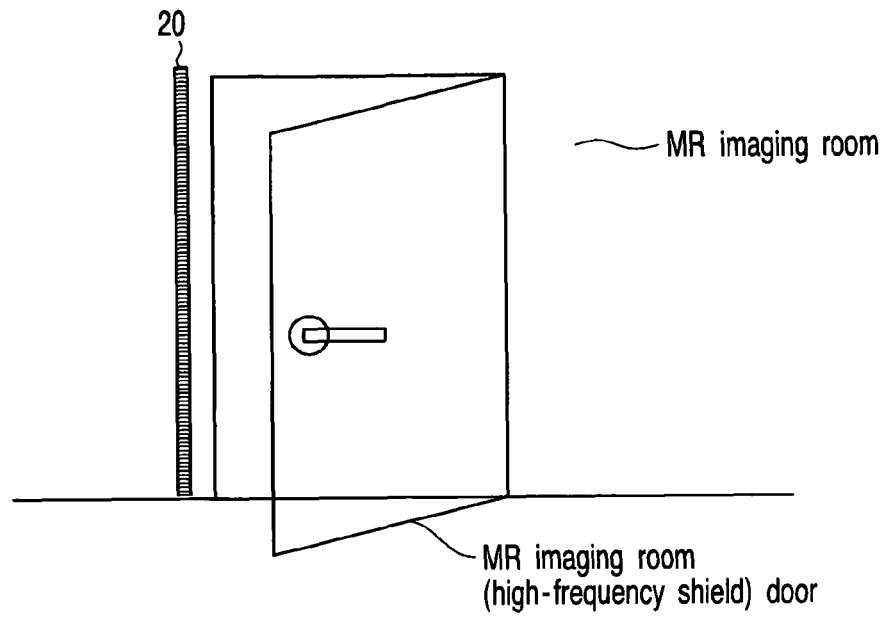
FIG. 3 is a view showing a scale near the door of an MR room in this embodiment.

2) A scale (height measure) 20 is bonded on a side of the door of the MR room, and the height of a patient is visually measured when he/she enters the room (FIG. 3).

Figure 4:
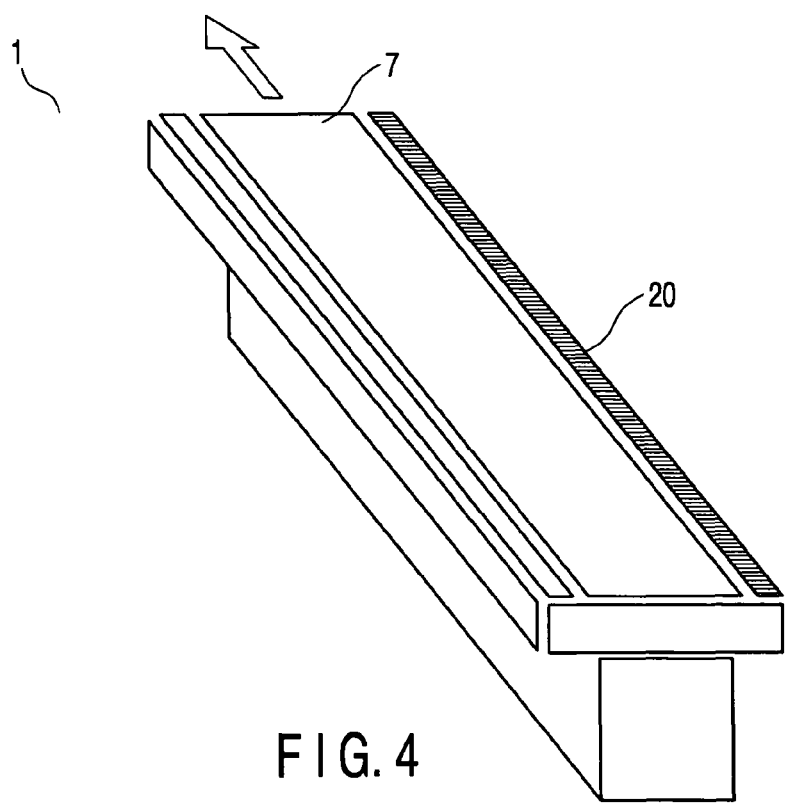
FIG. 4 is a view showing a scale on a bed portion in this embodiment.

3) The scale 20 is bonded on the surface of the bed top 7, and the height of the patient is visually measured when he/she is laid down on the bed (FIG. 4).

An imaging region is selected by the following method. As shown in FIG. 5, a target imaging region is selected from the representative drawings of imaging regions displayed on the screen of the display unit 14. Likewise, a pulse sequence is selected with the screen of the console or a switch, together with associated parameters.

The SAR value obtained from the weight, height, imaging region, and absorbed high-frequency output is displayed on the screen of the console, together with the type of SAR (whole body, partial body, head, or limbs), before the start of imaging operation in a selected pulse sequence. If the SAR value exceeds the upper limit value defined in the above safety standards, the corresponding information is displayed, and information indicating recommended changes of parameters for reducing the SAR value are also displayed. More specifically, the number of times of imaging operation is increased by decreasing the number of multi-slices, the slice thickness is increased, or another pulse sequence is selected. When a wide area is to be covered by a series of imaging operations as in the case of whole body imaging or lower limb imaging, the maximum value of partial body SAR obtained for each imaging region is displayed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance diagnostic apparatus comprising:
   an input unit configured to input information associated with a physique of a subject to be examined and information associated with an imaging region;
   a calculating unit configured to calculate a partial body SAR associated with a partial body including the imaging region on the basis of the input information associated with the physique and the input information associated with the imaging region; and
   a display unit configured to display the calculated partial body SAR,
   wherein, when imaging is divisionally performed a plurality of times for a wide area, the calculating unit which calculates the partial body SAR selects a maximum value of a plurality of partial body SARs associated with a plurality of body portions.

2. An apparatus according to claim 1, wherein the information associated with the physique includes a weight of the subject.

3. An apparatus according to claim 2, wherein the information associated with the physique includes a height of the subject.

4. An apparatus according to claim 3, wherein the weight and height of the subject are input as numerical values.

5. An apparatus according to claim 3, wherein the weight and height of the subject are selected from a plurality of height ranges.

6. An apparatus according to claim 1, wherein the calculating unit includes an estimating unit which estimates a partial weight of a partial body including the imaging region on the basis of the input information associated with the physique and the input information associated with the imaging region.

7. An apparatus according to claim 6, wherein the estimating unit which estimates the partial weight includes a storage unit which stores a table in which a standard partial weight is made to correspond to the physique and imaging region.

8. An apparatus according to claim 6, wherein the calculating unit includes a determining unit which determines a partial body SAR upper limit value on the basis of the estimated partial weight and the input information associated with the physique.

9. An apparatus according to claim 8, wherein the calculating unit includes a comparing unit which compares the calculated partial body SAR with the determined partial body SAR upper limit value.

10. An apparatus according to claim 9, wherein the display unit displays a message corresponding to a result of comparison between the calculated partial body SAR and the determined partial body SAR upper limit value.

11. An apparatus according to claim 10, wherein when the calculated partial body SAR exceeds the upper limit value, the display unit displays a message indicating that the calculated partial body SAR exceeds the upper limit value, together with information indicating a recommended change in imaging condition.

12. An apparatus according to claim 11, wherein the information indicating the recommended change includes a decrease in the number of multi-slices based on the pulse sequence.

13. An apparatus according to claim 11, wherein the information indicating the recommended change includes an increase in slice thickness based on the pulse sequence.

14. An apparatus according to claim 11, wherein the information indicating the recommended change includes a change in the pulse sequence.

15. An apparatus according to claim 8, wherein the display unit displays the determined partial body SAR upper limit value together with the calculated SAR.

16. An apparatus according to claim 1, wherein the estimating unit which estimates the partial weight calculates a whole body SAR in place of the partial body SAR when the height of the subject is not more than an axial length of a transmission high-frequency coil and the input imaging region is a chest or abdomen.

17. An apparatus according to claim 1, wherein when imaging is divisionally performed a plurality of times for a wide area, the calculating unit which calculates the partial body SAR calculates a partial body SAR for each imaging region.

18. An apparatus according to claim 1, wherein the input unit inputs selection of an arbitrary standard model from a plurality of standard models with different physiques as the physique.

19. An apparatus according to claim 1, which further comprises:
an unit configured to measure a transmission high-frequency output to the subject; and
an unit configured to control a pulse sequence to be applied to the subject, and
wherein the calculating unit calculates the partial body SAR calculates the partial body SAR on the basis of the partial weight, the transmission high-frequency output, and the pulse sequence.

20. An apparatus according to claim 1, wherein the information associated with the physique of the subject is received from an external patient database.

21. An apparatus according to claim 1, wherein the imaging region is selected from a plurality of region ranges.

22. An apparatus according to claim 1, further comprising a scale bonded to a bed portion on which the subject is to be placed.

23. An apparatus according to claim 1, further comprising a scale bonded near an entrance door of an MR imaging room.

24. A magnetic resonance diagnostic apparatus comprising:
an RF coil configured to generate an RF pulse;
a calculating unit configured to calculate a partial body SAR associated with a part of a subject to be examined which corresponds to a transmission range of the RF pulse which is unique to the RF coil; and
a display unit configured to display the calculated partial body SAR,
wherein, when imaging is divisionally performed a plurality of times for a wide area, the calculating unit which calculates the partial body SAR selects a maximum value of a plurality of partial body SARs associated with a plurality of body portions.

25. An apparatus according to claim 24, wherein the transmission range of the RF pulse is set to a range exceeding a predetermined strength in a spatial distribution concerning a coil center axis of a high-frequency electric field strength which is unique to the RF coil.

26. An apparatus according to claim 24, wherein the transmission range of the RF pulse is set to a half width in a spatial distribution concerning a coil center axis of a high-frequency electric field strength which is unique to the RF coil.

27. An apparatus according to claim 24, wherein the transmission range of the RF pulse is wider than the range reconstructing an image.

* * * * *